(12) United States Patent
Ponnampalam

(10) Patent No.: US 6,284,904 B1
(45) Date of Patent: Sep. 4, 2001

(54) PURIFICATION OF ORGANIC ACIDS USING ANION EXCHANGE CHROMATOGRAPHY

(75) Inventor: Elankovan Ponnampalam, Okemos, MI (US)

(73) Assignee: Michigan Biotechnology Institute, Lansing, MI (US)

( * ) Notice: Subject to any disclaimer, the term of this patent is extended or adjusted under 35 U.S.C. 154(b) by 0 days.

(21) Appl. No.: 09/623,253

(22) PCT Filed: Mar. 1, 1999

(86) PCT No.: PCT/US99/04408

§ 371 Date: Nov. 17, 2000

§ 102(e) Date: Nov. 17, 2000

(87) PCT Pub. No.: WO99/44707

PCT Pub. Date: Sep. 10, 1999

Related U.S. Application Data

(60) Provisional application No. 60/076,546, filed on Mar. 2, 1998.

(51) Int. Cl.[7] ............................. C11B 3/10; C11B 13/00; C07C 5/142
(52) U.S. Cl. ..................... 554/193; 554/175; 554/190; 562/513
(58) Field of Search ................................... 554/175, 190, 554/193; 562/573

(56) References Cited

U.S. PATENT DOCUMENTS

| | | | |
|---|---|---|---|
| 2,664,441 | 12/1953 | Owens et al. | 260/527 |
| 2,697,724 | 12/1954 | Collier | 260/527 |
| 3,015,655 | 1/1962 | Stark | 260/211.5 |
| 4,578,223 | 3/1986 | Cleary | 260/419 |
| 5,102,582 | 4/1992 | Zinnen | 554/190 |
| 5,179,219 | 1/1993 | Priegnitz | 554/193 |
| 5,362,895 | 11/1994 | Engelhardt et al. | 554/175 |
| 5,412,126 | 5/1995 | King et al. | 554/185 |

OTHER PUBLICATIONS

PCT International Search Report dated Nov. 1, 1999, in PCT Appln. No. PCT/US99/04408.

*Primary Examiner*—Deborah D. Carr
(74) *Attorney, Agent, or Firm*—Quarles & Brady LLP

(57) ABSTRACT

Disclosed is a cost-effective method for purifying and acidifying carboxylic acids, including organic acids and amino acids. The method involves removing impurities by allowing the anionic form of the carboxylic acid to bind to an anion exchange column and washing the column. The carboxylic anion is displaced as carboxylic acid by washing the resin with a strong inorganic anion. This method is effective in removing organic carboxylic acids and amino acids from a variety of industrial sources, including fermentation broths, hydrolysates, and waste streams.

15 Claims, 1 Drawing Sheet

PURIFICATION OF ORGANIC ACIDS USING ANION EXCHANGE CHROMATOGRAPHY

This Appln. is a 371 of PCT/US99/04408 filed Mar. 3, 1999 which claim benefit of Provisional No. 60/076,546 filed Mar. 2, 1998.

BACKGROUND OF THE INVENTION

Industrial fermentation broths, hydrolysates, and waste streams are a source of large amounts of carboxylic acids, including organic acids such as succinic acid and as well as amino acids. These carboxylic acids can be used in a number of important commercial applications.

For example, succinic acid is a four-carbon, dicarboxylic acid with the potential to become an important commodity chemical. Succinic acid can serve as an intermediate in the synthesis of many important intermediate and specialty chemicals for the consumer product industries. As a commodity chemical, succinic acid could replace many of the benzene class of commodity and intermediate petrochemicals, resulting in a large reduction of pollution from the manufacture and consumption of over 250 benzene derivative chemicals. Succinic acid is used as a food additive, plant growth stimulator, as an intermediate in the manufacture of pharmaceuticals, as well as polymers and resins for lacquers, dyes, and perfumes.

Currently, succinic acid is produced petrochemically from butane through maleic anhydride. Almost all of the succinic acid consumed in the United States is imported from overseas. Presently, the world market for succinic acid is 100 million pounds annually.

Succinic acid is co-produced in small quantities during corn fermentation in wet-milling ethanol production. It can also be produced from a variety of agricultural and forestry raw materials, such as starch crops and cellulosic sugars. Development of a cost-effective process for purifying this important compound from would provide more than 100 million bushels of an additional value-added commodity outlet for corn alone.

Methods exist for obtaining high purity carboxylic acids from fermentation broths. However, these methods involve numerous operations that make the process prohibitively expensive for commercialization.

One means by which carboxylic acids can be separated from other compounds such as sugars, for example, is through anion exchange chromatography. When unprotonated, the carboxyl group has a negative charge that allows ionic bonding with positively charged moieties on the anion exchange resin, and other materials are removed by washing the resin with water. Generally, the desired anions are released from the anionic exchange resin by washing the column with a solution of a base such as sodium hydroxide. However, this method causes the release of the molecule of interest in its salt form, rather than in its acid form. Therefore, if the acid form of the molecule is desired, it is necessary to include an acidification step and additional purification steps, which contributes significantly to the cost of purifying the acid. The commercial viability of using industrial fermentations, hydrolysates, and waste streams as a source of carboxylic acids depends upon a cost-effective means for recovering purified carboxylic acids from these sources.

What is needed in the art is a cost-effective method for the purification of carboxylic acids.

BRIEF SUMMARY OF THE INVENTION

The present invention is a method of purifying a carboxylic acid from a solution containing the carboxylic acid comprising the steps of: (a) applying the solution to an anionic exchange resin; (b) washing the resin under conditions that cause removal of neutral molecules, cations, large molecular weight compounds, and cell debris and allow retention of carboxylic anions on the resin; (c) displacing the carboxylic acid from the resin by washing the resin with an amount of a stronger anion effective to displace substantially all of the carboxylic acid; and (d) recovering the carboxylic acid in the eluant. In a preferred embodiment, the method of the present invention comprises regenerating the resin after the carboxylic acid displacement step by treating the resin with a strong base in an amount sufficient to allow substantial exchange of inorganic anion bound to the resin with hydroxide ions.

Depending on the particular properties of the carboxylic acids recovered by the method of the present invention, these compounds can be further purified or concentrated by any suitable method, including, but not limited to, crystallization or evaporative distillation.

In another embodiment, the present invention is a method for producing a purified ester from the corresponding carboxylic acid by eluting a carboxylic anion from an anion exchange resin with an alcohol comprising a suitable strong acid to produce the ester.

It is an object of the present invention to provide a cost-effective method for recovering and purifying carboxylic acids from solution.

It is an advantage that the method of the present invention is versatile and can be used with a wide variety of different carboxylic acids, including amino acids.

Other objects, features, and advantages of the present invention will become apparent on review of the specification.

DETAILED DESCRIPTION OF THE INVENTION

Figure 1:
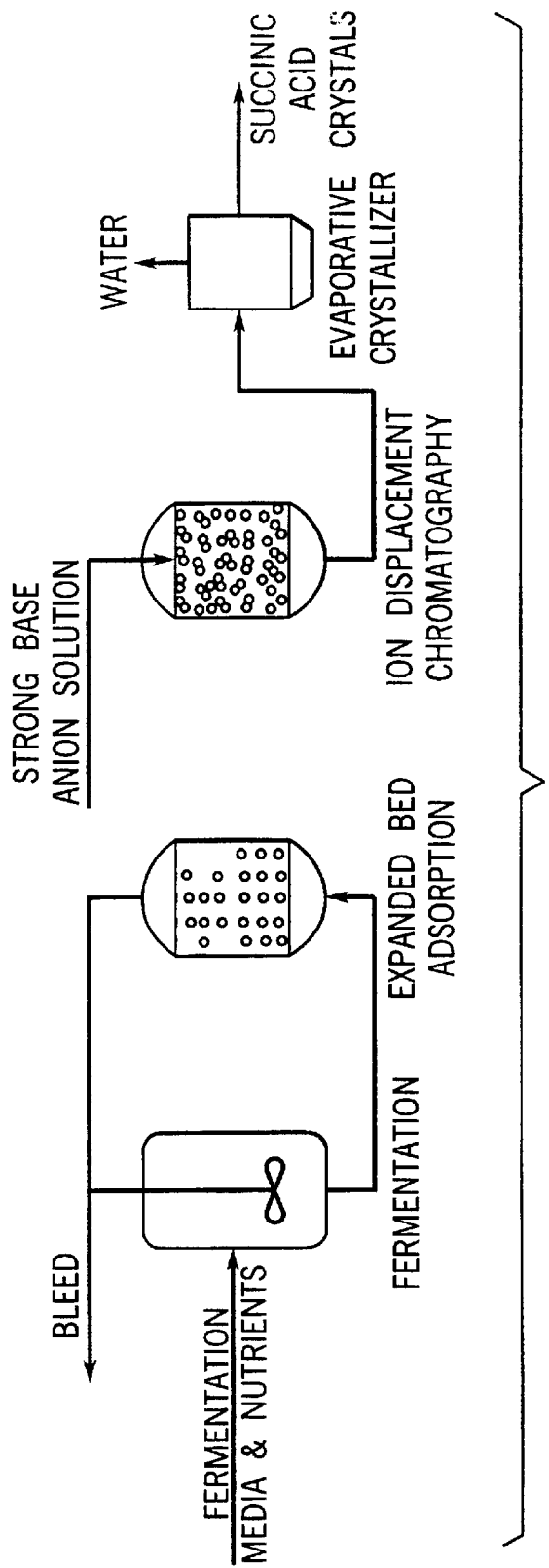
FIG. 1 is a schematic representation of the steps involved in purifying carboxylic acids using anion exchange chromatography.

The present invention is a method for purifying a carboxylic acid from a solution containing the carboxylic acid comprising the steps of: (a) applying the solution to an anionic exchange resin; (b) washing the resin under conditions that allow removal of materials present in the solution other than carboxylate anions; (c) displacing the carboxylic acid from the resin by washing the resin with an amount of a stronger anion effective to displace the carboxylic acid, and (d) recovering the carboxylic acid in the eluant.

The method of the present invention, which is based on expanded bed ion exchange technology, represents an improvement over standard methods in that it will allow the recovery of pure succinic acid crystals from fermentation broth at considerable cost savings because it employs fewer major unit operations.

In a preferred embodiment, the proposed operation allows the anion exchange resin to be recycled. The proposed exchange process is as follows. First, the carboxylic anion is adsorbed to a strong anion exchange resin by the formation of the ionic bonds between the carboxylic acid molecule and exchange sites on the resin. At this stage, most of the neutral or cationic material, or large molecules or cellular debris, pass through the resin. Next, the resin is washed with a liquid such as water to remove unbound contaminants that are trapped in the ion exchange resins. Following the wash step, carboxylic anions are displaced from the resin by exchanging the adsorbed carboxylic ion for a stronger, inorganic ion, thereby causing the release of carboxylic acid. The anion exchange resin is prepared for further cycles of carboxylic anion adsorption by regenerating the anion exchange sites on the resin. This is accomplished by treating the resin with a strong base, such as sodium hydroxide, which causes the inorganic anion to be exchanged for a hydroxide ion. The net result is an acidified, purified carboxylic acid product.

Anion exchange resins exist in salt or base forms. In order to adsorb the organic anion from organic salt mixture, the resin must be converted from the salt form to the base form during the regeneration procedure with sodium hydroxide. The steps of the purification process are as follows:

1) Regeneration of resin exchange sites

($R_z$=Resin)

2) Adsorption of carboxylate anion to resin

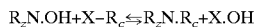

($R_c$=Carboxylic ion; X−=Inorganic)

3) Displacement and release of carboxylic ion as carboxylic acid

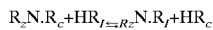

($HR_I$=Inorganic acid; $HR_c$=Carboxylic acid)

4) Release of inorganic anion and regeneration of resin

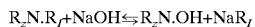

In the examples below, Rohm and Haas Amberlite IRA 900, 400, 458, or 440 anion exchange resins or Dow Chemical anion exchange resins were found to be effective in purifying carboxylic acid using the method of the present invention. One skilled in the art will appreciate that any strong base anion exchange resin could be used in the method of the present invention. A strong base anion exchange resin was chosen because this type of resin preferentially adsorbs anions (e.g., succinate or acetate), while allowing most sugars to pass through. Resin properties considered in the selection include the relative affinity of the resin for the targeted organic or amino acid ions versus other impurities, the capacity to adsorb carboxylic ions, and ability to release during displacement.

In the examples below, water was used during the wash step to remove unbound materials from the resin. However, any liquid that provides suitable wash conditions can be used in the wash step. Suitable wash conditions are conditions that allow removal of neutral or cationic molecules, large molecules, cellular debris, and cells, while at the same time allowing most of the bound carboxylate anions to be retained on the resin. Examples of other suitable washes include certain buffer solutions and solvents. A solution used as a wash in the present invention should have characteristics similar to water, in that it should be capable of removing substantially all unwanted materials, while allowing most of the anion to remain bound to the resin.

Optionally, when a dilute fermentation broth is used as the carboxylic anion source, the any cells or medium that pass through the resin may be returned to the fermentation tank or waste treatment tank.

The release step is conducted by using a strong inorganic acid at a concentration such that the number of equivalents applied to the column equals or, more preferably, exceeds the equivalents of carboxylate anion bound to the resin. By way of illustration, in the examples, 2.55 equivalents of succinate bound to an anion exchange resin was eluted with 2M $H_2SO_4$ (4 equivalents/L). In other examples, HCl was used to release the carboxylic anion as carboxylic acid. It is expected that other strong acids could also be used to release carboxylate ion as carboxylic acid, including, but not limited to, nitric acid, phosphoric acid, and certain polar amines.

After the carboxylic acid is removed from the resin, the product stream can be subjected to further purification. In the examples below, evaporative crystallization was employed to produce pure succinic acid crystals. However, any suitable purification method for purifying the carboxylic acid can be used in the present invention. For example, one could use distillation, extraction, elctrodialysis, and any other purification method to obtain purified organic or amino acids.

In addition to purifying carboxylic acids, the method of the present invention can be used to produce the corresponding esters in pure form. With the proper selection of ion exchange resin, an organic anion could be first adsorbed and then eluted with an alcohol to produce corresponding ester in pure form. Factors to consider in selecting the resin include its stability in the solvent to be used, its stability at increased temperatures, and its ability to release the anion when treated with the selected solvent. The selected ion exchange resin and the inorganic acid could be used as the esterification catalysts also.

The examples below demonstrate that succinic acid and acetic acid can be purified by the method of the present invention. One of skill in the art would appreciate that the method can be used to purify any carboxylic acid, including organic acids as well as amino acids.

In the examples below, the process was demonstrated to be effective in purifying carboxylic acids from fermentation broth, biomass hydrolysates, and dilute waste streams.

The following nonlimiting examples are intended to be purely illustrative.

EXAMPLES

Removal of Succinate from Fermentation Broth

| | | |
|---|---|---|
| Total mass of succinic acid in fermentation broth before ion exchange | = | 4 Kg |
| Volume of succinic acid broth before ion exchange | = | 4 L |
| Succinate concentration by HPLC | = | 58.14 g/L |
| Lactate concentration by HPLC | = | 5.05 g/L |
| Acetate concentration by HPLC | = | 3.89 g/L |
| Fermentation broth pH | = | |
| Mass of succinate solution (retentate) after ion exchange | = | 19.2 Kg |
| Volume of succinate solution (retentate) after ion exchange | = | 19.2 L |
| Succinate concentration by HPLC | = | 4.28 g/L |
| Lactate concentration | = | 0.23 g/L |
| Acetate concentration | = | 0.34 g/L |
| pH of the retentate | = | 9.3 |
| Ion exchange column bed volume | = | 7 L |
| Ion exchange column diameter | = | 4" |
| Flow rate | = | 21.6 L/hr |
| | = | 3 BV/hr |
| Total amount of succinate adsorbed on the ion exchange column | = | 58.14 × 4 − 4.28 × 19.2 |
| | = | 150.38 g |
| Total number of equivalents adsorbed | = | 150.38/59 |

| | | |
|---|---|---|
| on the ion exchange column | = | 2.55 eq |
| The adsorbence capacity of the ion exchange column in this run | = | 0.36 eq/L |
| Amount of lactate adsorbed to the column | = | 5.05 × 4 − 0.23 × 19.2 |
| Amount of acetate adsorbed to the column | = | 3.89 × 4 − 0.34 × 19.4 |
| | = | 8.96 g |

Displacement of Succinic Acid from Anion Exchange Resin

Succinate adsorbed ion exchange resin was eluted with approximately four liters $H_2SO_4$ (2M) and continued to be washed with about 20 liters of water. Two fractions were collected as the succinic acid products. These products were analyzed for the acid concentration.

| | | |
|---|---|---|
| Mass of fraction one elution | = | 5.2 Kg |
| Volume of fraction one | = | 5.2 L |
| Succinic acid concentration | = | 8.47 g/L |
| Lactic acid concentration | = | 0.14 h/L |
| Acetic acid concentration | = | 0.12 g/L |
| pH of the solution | = | 3.2 |
| Amount of succinate displaced from the ion exchange resin in the first fraction | = | 5.2 × 8.47 = 44.04 g |
| Mass of fraction two elution | = | 12.4 Kg |
| Volume of fraction two elution | = | 12.4 L |
| Succinate acid concentrations | = | 3.49 g/L |
| Lactic acid concentration | = | 0 |
| Acetic acid concentration | = | 0.02 |
| Amount of succinic acid displaced from the ion exchange resin in the second fraction | = | 12.4 × 3.49 = 42.16 g |
| Total mass of succinic acid displaced From the ion exchange resins | = | 44.04 + 42.16 = 86.2 g |
| Percentage of succinic acid eluted by The ion displacement process | = | 86.2/150.38 × 100 = 57.3% |
| Percentage of acetate eluted by this process | = | 5.2 × 0.12/8.96 × 100 = 7.2% |
| Percentage of lactate eluted by this process | = | 52. × 0.14/ 15.78 × 100 = 4.6% |

The above experiment showed that the succinic acid could be eluted as acid by selectively displacing the acid with another acid which has a lower $pK_a$ value, or a weak base anion may be exchanged by a strong base anion. This method allowed selective recovery of succinic acid over acetic and lactic acids. The pure succinic acid could be produced by crystallization. Further purification of succinic acid has been accomplished by evaporative crystallization, which yielded succinic acid crystals that are more than 99% pure. During the crystallization process the acetic acid could be recovered with vapor and lactic acid would stay in the mother liquor.

Removal of Acetate Ion from a Biomass Hydrolysate Containing Acetate and Sugars

| | | |
|---|---|---|
| Mass of acetate sugar solution before ion exchange | = | 81.6 Kg |
| Volume of acetate sugar solution before ion exchange | = | 81.6 L |
| Acetate concentration by HPLC | = | 4.53 g/L |
| Mass of acetate (retentate) after ion Exchange process | = | 96.2 Kg |
| Volume of acetate after ion exchange process | = | 96.2 L |
| Ion exchange column bed volume | = | 8.13 L |
| Ion exchange diameter | = | 4" |
| Flow Rate | = | 21 L/hr |
| | = | 2.58 BV/hr |
| Acetate concentration by HPLC | = | 1.73 g/L |
| Total amount of acetate adsorbed on the ion exchange column | = | 4.53 × 81.6 − 1.7. × 96.2 = 203.22 g |
| Total number of equivalents adsorbed on the ion exchange column | = | 203.22/60 = 3.38 eq |
| The exchange capacity of the ion exchange resin | = | 3.38 eq/8.13 L = 0.42 eq/L |

Displacement of Acetic Acid from Anion Exchange Resin

Acetate adsorbed ion exchange resin was eluted with four equivalent of a four liter sulfuric acid and continued to wash with water. Two fractions were collected as the acetic acid products. These products were analyzed by HPLC for its acid concentration.

| | | |
|---|---|---|
| Mass of fraction one product | = | 4.0 Kg |
| Volume of fraction one product | = | 4.0 L |
| Acetic acid concentration by HPLC | = | 9.65 g/L |
| Mass of acetic acid displaced in fraction one | = | 38.4 g |
| Mass of fraction two product | = | 3.8 Kg |
| Volume of fraction two product | = | 3.8 L |
| Acetic acid concentration | = | 39.8 g/L |
| Mass of acetic acid displaced in fraction two | = | 151.2 g |
| Total mass of acetic acid eluted from the ion exchange resin | = | 38.4 + 151.2 = 189.64 g |
| Percentage of acetic acid eluted by this process | = | 189.64/203.22 = 93.3% |

The above example showed that acetic acid could be recovered from salt solutions by selectively displacing the acetate ion with a stronger anion. In this example a weak base anion acetate ion was replaced by a stronger base anion sulfate ion. The acetic acid is further concentrated and purified by evaporative distillation.

Acetate Removal from High pH Waste Stream Collected During Ion Exchange Procedure Containing Acetate, Sugar and Sulfate

| | | |
|---|---|---|
| Mass of acetate solution before ion exchange | = | 49.0 Kg |
| Specific gravity | = | 1.012 |
| Volume of the solution before ion exchange | = | 49.0 × 1.012 = 49.59 L |
| Concentration of acetate by HPLC | = | 1.99 g/L |
| Concentration of sulfate by HPLC | = | 5.19 g/L |
| Concentration of glucose by HPLC | = | 2.75 g/L |
| Initial pH of the solution | = | 9.33 |
| Ion exchange column bed volume | = | 7 L |
| Ion exchange column diameter | = | 4" |
| Flow rate | = | 21.6 L/hr |

-continued

|  |  |  |
|---|---|---|
|  | = | 3 BV/hr |
| Mass of the acetate (retentate) after ion exchange process | = | 60.6 Kg |
| Specific gravity | = | 1.005 |
| Volume of the retentate | = | 60.90 L |
| Final pH of the solution | = | 11.5 |
| Acetate concentration after ion exchange | = | .38 g/L |
| Sulfate concentration after ion exchange | = | 1.44 g/L |
| Sugar concentration after ion exchange | = | 2.19 g/L |
| Total acetate adsorbed on the ion exchange resin | = | 49.59 × 1.99 − 60.9 × 0.38 |
|  | = | 75.54 g |
| Total sulfate adsorbed on the column | = | 49.59 × 5.19 − 60.9 × 1.44 |
|  | = | 169.68 |
| Number of equivalents adsorbed on the ion exchange column | = | 75.54/60 + 169.68/49 |
|  | = | 4.72 eq |

Displacement of Acetic Acid from Anion Exchange Resin

Acetate adsorbed ion exchange resin was eluted with two equivalent to a four liter sulfuric acid and continued to wash with water. Two fraction were collected as the acetic acid products. These products were analyzed by HPLC for its acetic acid concentration.

|  |  |  |
|---|---|---|
| Mass of fraction one elution | = | 20 Kg |
| Volume of the acid displacement | = | 20 L |
| Acetic acid concentration | = | 2.11 g/L |
| pH of the solution | = | 3.2~5.0 |
| Amount of acetic acid removed | = | 2.11 × 20 |
|  | = | 42.4 g |
| Percentage of acetate eluted by this Process | = | 42.4/75.54 × 100 |
|  | = | 55.86% |

No sulfuric acid, and very little sugar is eluted during this process. The acetic acid is easily concentrated and purified by evaporative distillation or steam stripping. This food grade acetic acid is produced from a natural source or biomass, not synthesized from a petroleum source.

Resin Regeneration for Purification of Lactic Acid, Succinic Acid, and Citric Acid For the purification of lactic acid, succinic acid, and citric acid as described in the examples that follow, two one-inch diameter, four-foot tall, approximately 500 ml bed volume columns were used for the ion exchange.

Initially, the columns were regenerated with a 4% NaOH solution at the flow rate of 2 bed volumes (BV) per hour with 2–3 bed volumes of sodium hydroxide solution.

The regenerated column was washed with four bed volumes of deionized water at a flow rate of 2 BV per hour and with two bed volumes of deionized water at a higher flow rate. This water wash washed out substantially all of the unadsorbed sodium hydroxide solution from the column. At this time, the column was ready for the adsorption cycle.

Lactate Ion Adsorption and Displacement

The first purification was conducted with a 10% (approximate) lactic salt solution, which was passed through the column for two hours at a flow rate of one bed volume pr hour. The lactate-depleted solution was collected and analyzed for lactic concentration. Then the column was washed with two bed volumes of water. The lactic ion was displaced with a 4% HCl solution at a flow rate of one bed volume per hour. The displaced lactic acid solution was collected and analyzed for lactic acid concentration by HPLC. The eluted solution is a lactic acid solution produced from lactate salt. Pure lactic acid could be produced from this dilute solution by evaporation crystallization.

The following calculations show the amount of dilute acid produced from salts by anion exchange chromatography.

| Adsorption cycle: |  | Run I | Run II |
|---|---|---|---|
| Total mass of lactate fed through column | = | 721 g | 865 g |
| Initial lactic concentration | = | 82 g/L | 82 g/L |
| Mass of depleted lactic Solution collected at The bottom of the column | = | 784 g | 827 g |
| Lactic concentration in Depleted solution | = | 0 g/L | 0 g/L |
| Mass of lactic ion adsorbed by the column (Assumed 1 ml solution = 1 g) | = | $\frac{721 \times 82}{1000}$ | $\frac{865 \times 82}{1000}$ |
|  | = | 59 g | 70 g |
| Displacement cycle: |  | Run I | Run II |
| Mass of dilute acid solution collected at the end of displacement cycle | = | 1383 g | 1498 g |
| Lactic acid concentration in the displaced solution | = | 29 g/L | 29 g/L |
| Total mass of lactic acid displaced | = | $\frac{1383 \times 29}{1000}$ | $\frac{1489 \times 29}{1000}$ |
|  | = | 40 g | 43 g |
| Percentage of lactic acid displaced by this anion exchange procedure | = | $\frac{43 \times 100}{59}$ | $\frac{43 \times 100}{70}$ |
|  | = | 59% | 61% |

These results demonstrate that lactic acid can be purified as lactic acid by anion exchange chromatography.

Succinate Ion Adsorption and Displacement Calculation

Succinic acid was purifed from a dilute salt solution using the procedures described above for lactic acid purification.

The following calculations show the amount of dilute acid produced from salts by anion exchange chromatography.

| Absorption cycle: |  | Run I | Run II |
|---|---|---|---|
| Total mass of succinate passed through the columns | = | 1093 g | 1334 g |
| Initial succinic concentration | = | 100 g/L | 100 g/L |
| Mass of depleted succinc solution collected at the bottom of the column | = | 1040 g | 1242 g |
| Succinic concentration in the Depleted solution | = | 0 g/L | 0 g/L |

-continued

| | | Run I | Run II |
|---|---|---|---|
| Mass of succinic ions adsorbed By the ion exchange resins (Assumed 1 ml Solution = 1 g) | = | $\frac{1093 \times 100}{1000}$ | $\frac{1334 \times 100}{1000}$ |
| | = | 109.3 g | 133.4 g |
| Displacement cycle: | | Run I | Run II |
| Mass of dilute acid solution collected at the end of the displaced solutions | = | 1357 g | 998 g |
| Succinic acid concentration of the displaced solutions | = | 54.5 g/L | 53.5 g/L |
| Total mass of succinic acid displaced | = | $\frac{1357 \times 54.5}{109.3}$ | $\frac{53.4 \times 100}{133.4}$ |
| | = | 67.7% | 40% |

The above example showed that succinic acid could be produced as succinic acid from succinate solution by anion exchange chromatography. Pure Succinic acid crystals can be produced from this solution by evaporative crystallization.

Citrate Ion Adsorption and Displacement

Citric acid was purifed from a dilute salt solution using the procedures described above for lactic acid purification.

The following calculations show the amount of dilute acid produced from salts by anion exchange chromatography.

| Adsorption cycle: | | Run I | Run II |
|---|---|---|---|
| Total mass of citrate passed through the column | = | 869 g | 954 g |
| Initial citric concentration | = | 64 g/L | 66 g/l |
| Mass of citrate depleted solution collected at the bottom of the column | = | 829 g | 920 g |
| Citric concentration in the depleted solution | = | 0 g/L | 0 g/L |
| Mass of citric ions adsorbed by the ion exchange resins (assumed 1 ml solution = 1 g) | = | $\frac{869 \times 64}{1000}$ | $\frac{954 \times 64}{1000}$ |
| | = | 55.6 g | 61 g |
| Displacement cycle: | | Run I | Run II |
| Mass of dilute acid solution collected at the end of the displacement cycle | = | 2077 g | 1869 g |
| Citric acid concentration of the displaced solution | = | 23 g/L | 29 g/L |
| Total mass of citrate acid displaced | = | $\frac{2077 \times 23}{1000}$ | $\frac{1869 \times 29}{1000}$ |
| | = | 47.7 g | 54 g |
| Percentage of citric acid displaced by this anion exchange procedure | = | $\frac{47.7 \times 100}{55.6}$ | $\frac{54 \times 100}{61}$ |
| | = | 86% | 88.5% |

The above example demonstrate that citric acid can be purified as citric acid from a citrate solution by anion exchange chromatography. Pure citric acid crystals can be produced from this displaced acid solution by evaporative crystallization or other procedure.

The above examples demonstrate that an organic acid can be produced as organic acid from a dilute organic salt mixture by anion exchange chromatography.

In the same way, an unprotonated anion of an organic acid can be adsorbed, purified and displaced in the acid form by anion exchange chromatography from dilute fermentation broth, hydrolysate solution or dilute wast streams.

Also, amino acids and other charged compounds could be adsorbed, purified and displaced by this chromatography procedure by selecting the ion exchange resin and displacement solution.

This procedure may be optimized by selecting the proper ion exchange resin displacement solution and concentrations displacement solution.

The above examples show that organic acids (acetic, succinic, lactic, citric, etc.) can be purified from fermentation broths, biomass hydrolysates or from dilute waste streams by ion exchange chromatography and acidified and displaced by a stronger acid or strong base anion. The product is recovered as a pure acid form, as opposed to the salt form. The nonionic impurities are removed from the product by this method.

The present invention may be used to recover carboxylic acids from a fermentation reaction in which the carboxylic acid is produced as a secondary byproduct (e.g., succinate is produced during ethanol production by the fermentation of corn) or as the primary product of the fermentation reaction (certain microorganisms produce particular carboxylic acids such as succinic acid, acetic acid, or pyruvic acid in relatively large amounts).

Numerous bacterial and fungal isolates capable of producing large quantities of particular carboxylic acids under certain growth conditions are known to the art. One wishing to purify a particular carboxylic acid in large quantities could readily do so using the teachings of the present invention by selecting a microorganism that is capable of producing the desired carboxylic acid under certain growth conditions, culturing the microorganism under those conditions, and recovering the carboxylic acid from the medium using the method disclosed herein.

By way of example, one wishing to isolate succinate could do so by culturing an organism such as Anaerobiospirillum succiniciproducens (ANS) ATCC 29305 in a glucose containing medium at a pH of 5.9–6.4, and with an excess of $CO_2$. To further increase succinate yield by reducing carbon loss to acetic acid production, one could use an acetate-negative mutant, such as ANS 53488.

The present invention is not limited to the exemplified embodiments, but is intended to encompass all such modifications and variations as come within the scope of the following claims.

I claim:

1. A method for recovering a carboxylic acid from a carboxylic acid-containing solution comprising the steps of:
   (a) contacting the carboxylic acid-containing solution with an anionic exchange resin;
   (b) washing the resin under suitable conditions to remove materials other than carboxylate anions;
   (c) displacing the carboxylate anion from the resin as carboxylic acid by washing the resin with the acid form of an inorganic anion, or an anion that is stronger than the carboxylate anion, in an amount effective to displace the carboxylate anion the corresponding carboxylic acid; and
   (d) collecting fractions containing carboxylic acid.

2. The method of claim 1, wherein the carboxylic acid-containing solution is selected from the group consisting of a fermentation broth, a biomass hydrolysate, a dilute solution of a salt form of the corresponding carboxylate anion, and a waste stream.

3. The method of claim 1, further comprising the step of purifying the carboxylic acid from the carboxylic acid-containing fraction of step (d).

4. The method of claim 3, wherein the purification step is selected from the group consisting of crystallization and distillation.

5. The method of claim 1, wherein the contacting step is accomplished by applying the carboxylic acid-containing solution to a fixed bed anion exchange resin.

6. The method of claim 1, wherein the contacting step is accomplished by passing a fluidized resin bed through the carboxylic acid-containing solution.

7. The method of claim 1, wherein the displacing wash of step (c) the acid form of an anion that is stronger than the carboxylate anion of step (c).

8. The method of claim 1, wherein the displacing wash of step (c) comprises the acid form of an inorganic anion.

9. The method of claim 7, wherein the displacing wash of step (c) comprises a polar amine.

10. The method of claim 2, wherein the carboxylic acid-containing solution is a fermentation broth.

11. The method of claim 2, wherein the carboxylic acid-containing solution is a biomass hydrolysate.

12. The method of claim 2, wherein the carboxylic acid-containing solution is a waste stream.

13. The method of claim 2, wherein the carboxylic acid-containing solution is a dilute solution of a salt form of the corresponding carboxylate anion.

14. A method of producing an ester from a carboxylic acid-containing solution comprising the steps of:

(a) contacting the carboxylic acid-containing solution with an anionic exchange resin;

(b) washing the resin under suitable conditions to remove materials other than carboxylate anions;

(c) displacing the carboxylate anion from the resin as carboxylic acid by washing the resin with an alcohol comprising the acid form of an inorganic anion, or an anion that is stronger than the carboxylate anion, in an amount effective to displace the carboxylic acid; and (d) collecting fractions the ester.

15. The method of claim 14, further comprising the step of purifying the ester of step (d).

* * * * *

UNITED STATES PATENT AND TRADEMARK OFFICE
CERTIFICATE OF CORRECTION

PATENT NO. : 6,284,904 B1
DATED : September 4, 2001
INVENTOR(S) : Ponnampalam, Elankovan It is certified that error appears in the above-identified patent and that said Letters Patent is hereby corrected as shown below:

Column 1,
Line 3, please add:
-- STATEMENT REGARDING FEDERALLY SPONSORED RESEARCH OR DEVELOPMENT
    This invention was made with Government support under NREL Subcontract No. XXE-9-29058-01, Prime Contract No. DE-AC36-98GO10337 awarded by the Department of Energy. The Government has certain rights in this invention. --

Signed and Sealed this

Fifteenth Day of July, 2003

JAMES E. ROGAN
*Director of the United States Patent and Trademark Office*